United States Patent [19]

Nagy née Kricsfalussy et al.

[11] Patent Number: 5,169,847
[45] Date of Patent: Dec. 8, 1992

[54] DRUG SOLUTIONS OF INCREASED STABILITY AND WITHOUT TISSUE-DAMAGING EFFECT AND PROCESS FOR PREPARING SAME

[75] Inventors: Margit Nagy née Kricsfalussy; Szauder née Laukó ; János Egri, all of Budapest, Hungary

[73] Assignee: Egis Gyógyszergyár, Budapest, Hungary

[21] Appl. No.: 797,963

[22] Filed: Nov. 26, 1991

[30] Foreign Application Priority Data

Nov. 27, 1990 [HU] Hungary ............................. 7654/90

[51] Int. Cl.$^5$ .............................................. A61K 31/54
[52] U.S. Cl. ................... 514/226.5; 514/912
[58] Field of Search .................... 514/301, 226 S, 912

[56] References Cited

PUBLICATIONS

Chemical Abstract 94:15618X (1981), Tighineanu et al.

Primary Examiner—Frederick E. Waddell
Assistant Examiner—Zohreh A. Fay
Attorney, Agent, or Firm—Beveridge, DeGrandi & Weilacher

[57] ABSTRACT

The invention relates to novel pyroxycam solutions of increased stability and without tissue-damaging effect, particularly to solutions which can be used as injectable solutions or eye drops.

The solution according to the invention comprises 1 to 5% by mass of 4 hydroxy- 2-methyl-N-(2-pyridyl)-2H-1,2-benzothiazine-3-carboxamide-1,1-dioxide, 0.5 to 5.0 % by mass of sodium glycinecarboxylate as well as 0.5 to 12% by mass of additive(s).

The invention further relates to a process for the preparation of the above solutions.

4 Claims, No Drawings

DRUG SOLUTIONS OF INCREASED STABILITY AND WITHOUT TISSUE-DAMAGING EFFECT AND PROCESS FOR PREPARING SAME

This invention relates to novel pyroxycam solutions of increased stability and without tissue-damaging effect, particularly to solutions which are useful for injection or eye drops. The invention further relates to a process for preparing these solutions.

Pyroxycam, chemically 4-hydroxy-2-methyl-N-(2-pyridyl)-2H-1,2-benzothiazine-3-carboxamide-1,1-dioxide is an effective antiinflammatory drug which is administered mainly orally in capsule form to the patients. However, the topic injection treatment results in a more rapid improvement in various inflammations of locomotor organs; therefore, there exists a demand also on injectable solutions containing pyroxycam as active ingredient. Of course, topic treatment by using eye drops containing piroxycam similarly leads to more advantageous results on patients suffering from eye imflammations.

The preparation of stable aqueous solutions is hindered by the poor water-solubility of pyroxycam. Thus, an aqueous suspension of pyroxycam is used as eye drop composition according to the Belgian patent specification No. 899,587. The suspension of the active ingredient (drug) for injections or eye drops is disadvantageous.

It has been tried to increase the solubility by salt formation with the 4-hydroxy group of pyroxycam. According to the published German patent application No. 3,437,232 2 % by mass of pyroxycam are dissolved at a pH value of 8 to 9 in a mixture of propylene glycol, ethanol and water by adding D-(−)-N-methylglucamine. The drawback of this known injectable solution lies in that a part of the active ingredient precipitates from the solution during prolonged storage. In addition, when the composition is intramuscularly administered, a tissue-damaging effect is caused by the propylene glycol being present in a concentration of about 40 % by mass.

According to the published European patent application No. 66,458 a powder ampoule is prepared from the salt of pyroxycam formed with lysine or arginine, which is dissolved in distilled water immediately before administration. This known composition is not suitable for being used as an eye drop. The preparation of the powder ampoule in itself is relatively expensive and the work of the physician also becomes cumbersome by the preparation of the solution to be injected.

According to the published German patent application No. 3,217,315 a pyroxycam salt is formed with an alkylglucamine, which is then dissolved in a mixture of polyethylene glycol, N,N-dimethylacetamide and water while heating. The obtained solution containing an organic solvent and having a pH value of 9 to 10 exerts a tissue-irritating action when administered intramuscularly and cannot be used as an eye drop.

The aim of the present invention is to provide a pyroxycam solution of increased stability and being free from any tissue-damaging effect.

Now it has been found that this aim can be achieved and a composition being useful both for injection as well as eye drop can be obtained if a solution is used which comprises 1 to 5 % by mass of 4-hydroxy-2-methyl-N-(2-pyridyl)-2H-1,2-benzothiazine-3-carboxamide-1,1-dioxide, 0.5 to 5% by mass of sodium glycinecarboxylate of the formula $$Na^+ {}^-OOC\text{-}NH\text{-}CH_2\text{-}COO^- H_3^+N\text{-}CH_2\text{-}COO^-Na^+$$

and 0.5 to 12% by mass of additive(s), preferably viscosity-increasing, surface-active and chelating agents commonly used for the preparation of liquid drug formulations.

The thus-obtained aqueous solution containing 1 to 5% by mass of pyroxycam, having a pH value of 8 to 9, remains stable at room temperature for at least 2 years and does not exert any tissue-damaging effect after parenteral, e.g. intramuscular or subcutaneous, administration.

Thus the invention relates to a process for preparing the above composition, which comprises dissolving in water at 80° to 100° C. 1 to 5% by mass of 4-hydroxy-2-methyl-N-(2-pyridyl)-2H-1,2-benzothiazine-3-carboxamide-1,1-dioxide, 0.5 to 5% by mass of sodium glycinecarboxylate and 0.5 to 12% by mass of additive(s), preferably viscosity-increasing, surface-active and chelating agents commonly used for the preparation of liquid drug formulations.

Viscosity-increasing and surface-active agent(s) and a chelating substance are mainly employed as additives commonly used for the preparation of liquid drug formulations.

The viscosity-increasing agent(s), e.g. polyvinylpyrrolidone, methylcellulose, hydroxypropylcellulose, carboxymethylcellulose sodium salt, gelatine, cellulose glycolate, sorbitol and the like are usually present in a total amount of 1 to 10% by mass in the composition. The surface-active agent(s), e.g. a polyglycol ether such as polyethyleneglycol-nonylphenol ether as well as polyethylene glycol sorbitan monolaurate, polyethylene glycol sorbitan monooleate, polyethylene glycol sorbitan monooleate, polyethylene glycol stearate, polyethylene glycol polypropylene glycol ether and the like are mostly used in a total amount of 0.01 to 1.0% by mass.

It is suitable to use disodium ethylenediaminetetraacetate usually in an amount of 0.01 to 0.1% by mass as a chelating agent.

Particularly in the preparation of eye drops, bacteriostatic agent(s) such as 1,1,1-trichloro-2-methyl-2-propanol, cetylpyridinium chloride, methyl 4-hydroxybenzoate, propyl 4-hydroxybenzoate, sodium S-[ethylmercury(II)]thiosalicylate and the like may be incorporated to the composition as additives maintaining the sterility of the solution. These agents are commonly used in a total amount of 0.0001 to 0.05% by weight.

According to the process of the invention the pyroxycam solution with an increased stability and without tissue-damaging effect is prepared by dissolving the additives commonly used for the preparation of liquid drug formulations and sodium glycinecarboxylate at a temperature between 90° C. and 100° C. in the main bulk of the required amount of distilled water and then dissolving the pyroxycam at 90° to 100° C. in the obtained solution. After complete dissolution the final volume of the solution is adjusted by adding distilled water. Thereafter, the solution is filtered through a filter with small pore-size and filled into ampoules for injectable solutions or into glass-droppers for eye drops. After sealing the ampoules are sterilized by heat.

Samples for the pyroxycam solution prepared according to Example 1 are being stored since 2 years. No precipitation of solid material has been observed, nor have been altered the quality characteristics (colour, pH, active-ingredient content) of the solution. Thus, the solution prepared according to the invention can be maintained without any damage for at least 2 years.

The toxicity of the pyroxycam solution prepared according to Example 1 was studied on rats by intramuscular administration. No perishment occurred during an observation period of 14 days following administration of a dose of 1, 2, 5 or 8 ml/kg, respectively. Thus, the $LD_{50}$ value of the solution is higher than 8 ml/kg, i.e. higher than 160 mg/kg as expressed in the amount of the active ingredient. It is noted for comparison that the $LD_{50}$ value of a known solution containing 2% by weight of pyroxycam, 2% by weight of benzyl alcohol, 3% by weight of nicotineamide, 40% by weight of propylene glycol and distilled water was found to be 160 mg/kg.

A tissue-tolerability examination was also carried out on rats by subcutaneous administration of the pyroxycam solution prepared according to Example 1. Three male and three female rats were injected 0.3 ml of the solution each. No tissue-damaging effect was observed during an observation period of 14 days. Thus, the solution does not cause any tissue-damaging effect after adminstration by injection.

The process according to the invention provides a pyroxycam solution which is simple to prepare, possesses high stability, is free from any tissue-damaging effect and is suitable both for injection as well as for use as an eye-drop composition.

The invention is illustrated in detail by the following non-limiting Examples.

EXAMPLE 1

0.30 g of disodium ethylenediaminetetraacetate, 50 g of polyvinylpyrrolidone (Kollidon PF 12) and 17 g of sodium glycinecarboxylate are dissolved in 900 of ml water at the boiling point. After adding 20 g of pyroxycam and dissolving it in the solution at a temperature between 90° C. and 100° C. while stirring the solution by bubbling through gaseous nitrogen until complete dissolution, the solution is filled up to a volume of 1000 ml with distilled water and homogenized. The solution showing a pH value of 8.5 is filtered through a filter sheet with 0.45 /um pore-size and then filled into ampoules of 1 ml volume each. After sealing the ampoules are sterilized at 120° C. for 20 minutes.

EXAMPLE 2

5 g of polyvinylpyrrolidone, 0.03 g of disodium ethylenediaminetetraacetate, 0.1 g of Pluronic(®) F-68 (polyethylene glycol polypropylene glycol ether; manufacturer: Wyandotte), 1.7 g of sodium glycinecarboxylate and 0.0001 g of sodium S-[ethyl- mercury(II)]thiosalicylate are dissolved in 90 ml of distilled water at 80° to 120° C., then 2 g of pyroxycam are dissolved at 90° to 100° C. in the solution obtained while stirring by bubbling gaseous nitrogen through the solution. The clear solution is filled up to a volume of 100 ml with distilled water, homogenized and filled into glass-droppers of 10 ml volume each. The solution obtained can be used as an eye-drop composition.

EXAMPLE 3

A solution containing the components listed hereinafter is prepared as described in Example 2.

| Components | % by mass |
|---|---|
| Pyroxycam | 5.0 |
| Disodium ethylenediaminetetraacetate | 0.1 |
| Sodium glycinecarboxylate | 2.4 |
| Pluronic ® F-68 | 0.5 |
| Polyvinylpyrrolidone | 10.0 |
| Sodium S-[ethyl-mercury(II)]thiosalicylate | 0.01 |
| Distilled water q.s.   up to | 100.00 |

The solution obtained can be used as an eye-drop composition.

We claim:

1. A pyroxycam solution of increased stability and without tissue-damaging effect, which comprises 1 to 5% by mass of 4-hydroxy-2-methyl-N-(2-pyridyl)-2H-1,2-benzothiazine-3-carboxamide-1,1-dioxide, 0.5 to 5% by mass of sodium glycinecarboxylate as well as 0.5 to 12.0% by mass of additives.

2. A pyroxycam solution as claimed in claim 1, in which the additives are viscosity-increasing, surface-active and/or chelating agents commonly used for the preparation of liquid drug formulations.

3. A process for the preparation of a pyroxycam solution with an increased stability and without tissue-damaging effect as claimed in claim 1, which comprises dissolving in water at 80° to 100° C. 1 to 5% by mass of 4-hydroxy-2-methyl-N-(2-pyridyl)-2H-1,2-benzothiazine-3-carboxamide-1,1-dioxide, 0.5 to 5% by mass of sodium glycinecarboxylate and 0.5 to 12.0% by mass of additive(s), preferably viscosity-increasing, surface active and chelating agents commonly used for the preparation of liquid drug formulations.

4. A process as claimed in claim 1, in which viscosity-increasing, surface-active and/or chelating agents commonly used for the preparation of liquid drug formulations are used as additives.

* * * * *